United States Patent
Allred et al.

(10) Patent No.: US 7,074,042 B2
(45) Date of Patent: *Jul. 11, 2006

(54) TRAY-LIKE DENTAL BLEACHING DEVICES HAVING A BARRIER LAYER AND A SUBSTANTIALLY SOLID BLEACHING COMPOSITION

(75) Inventors: Peter M. Allred, Riverton, UT (US); Neil T. Jessop, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 434 days.

This patent is subject to a terminal disclaimer.

(21) Appl. No.: 10/446,235

(22) Filed: May 27, 2003

(65) Prior Publication Data

US 2004/0241615 A1    Dec. 2, 2004

(51) Int. Cl.
*A61C 15/00*    (2006.01)
*A61K 9/20*    (2006.01)
(52) U.S. Cl. .......................... 433/216; 424/53; 433/215
(58) Field of Classification Search ................ 433/80, 433/215, 216; 424/53; 206/63.5, 369
See application file for complete search history.

(56) References Cited

U.S. PATENT DOCUMENTS

| 165,584 | A | 7/1875 | Hopfen |
| 1,637,153 | A | 7/1927 | Lawton |
| 2,257,709 | A | 9/1941 | Anderson .................... 128/260 |
| 2,835,628 | A | 5/1958 | Saffir ............................ 167/84 |
| 3,339,547 | A | 9/1967 | Drabkowski ................. 128/260 |
| 3,527,219 | A | 9/1970 | Greenberg ................... 128/260 |
| 3,577,640 | A | 5/1971 | Lee ................................ 32/32 |
| 3,624,909 | A | 12/1971 | Greenberg ...................... 32/40 |
| 3,688,406 | A | 9/1972 | Porter et al. ................. 32/40 R |
| 3,955,281 | A | 5/1976 | Weitzman .................... 32/14 B |
| 4,044,762 | A | 8/1977 | Jacobs ......................... 128/136 |
| 4,063,552 | A | 12/1977 | Going et al. ................ 128/136 |
| 4,064,628 | A | 12/1977 | Weitzman .................... 32/14 B |

(Continued)

FOREIGN PATENT DOCUMENTS

| WO | WO 88/06869 | 9/1988 |
| WO | WO 03/000216 | 1/2003 |

OTHER PUBLICATIONS

Technical Bulletin: Hydrogen Peroxide-Polyvinylpyrrolidone Polymer Complexes, International Specialty Products, 1361 Alps Road, Wayne New Jersey 07470, www.ispcorp.com (Dec. 2003).

*Primary Examiner*—Todd E. Manahan
(74) *Attorney, Agent, or Firm*—Workman Nydegger

(57) ABSTRACT

Dental bleaching devices in the shape of a dental tray or tray-like form include an outer barrier layer and an inner bleaching layer. The bleaching layer comprises a substantially solid dental bleaching composition that has increased adhesiveness to teeth when moistened with saliva or water. The shape of the dental bleaching device facilitates placement of the device over a person's teeth with substantially less manipulation compared to the use of initially flat bleaching strips. The substantially solid dental bleaching composition becomes more adhesive when moistened with saliva or water, yet remains intact and coherent after the dental bleaching device is placed over a person's teeth during bleaching. The result is that the moistened dental bleaching composition is able to reliably adhere the dental bleaching device against a user's teeth during a bleaching procedure. However, because a substantial portion of the dental bleaching composition remains solid or semi-solid during bleaching, the bleaching composition maintains a substantial portion of its adhesive properties and internal cohesive strength.

53 Claims, 6 Drawing Sheets

U.S. PATENT DOCUMENTS

| | | | |
|---|---|---|---|
| 4,138,814 A | 2/1979 | Weitzman | 32/14 B |
| RE33,093 E | 10/1989 | Schiraldi et al. | 424/676 |
| 4,900,721 A | 2/1990 | Bansemir | |
| 4,902,227 A | 2/1990 | Smith | 433/215 |
| 5,008,093 A | 4/1991 | Merianos | |
| 5,051,476 A | 9/1991 | Uji et al. | 525/186 |
| 5,085,585 A | 2/1992 | Zimble | 433/80 |
| 5,108,742 A | 4/1992 | Merianos | |
| 5,112,225 A | 5/1992 | Diesso | 433/48 |
| 5,183,901 A | 2/1993 | Login et al. | |
| 5,211,559 A | 5/1993 | Hart et al. | 433/80 |
| 5,310,563 A | 5/1994 | Curtis et al. | 424/616 |
| 5,326,685 A | 7/1994 | Gaglio et al. | 433/215 |
| 5,346,061 A | 9/1994 | Newman et al. | 206/221 |
| 5,356,291 A | 10/1994 | Darnell | 433/216 |
| 5,376,006 A | 12/1994 | Fischer | 433/215 |
| 5,425,953 A | 6/1995 | Sintov et al. | 424/404 |
| 5,562,449 A | 10/1996 | Jacobs et al. | 433/215 |
| 5,573,399 A | 11/1996 | McClintock, II | 433/80 |
| 5,575,654 A | 11/1996 | Fontenot | 433/215 |
| 5,611,687 A | 3/1997 | Wagner | 433/80 |
| 5,616,027 A | 4/1997 | Jacobs et al. | 433/37 |
| 5,631,000 A | 5/1997 | Pellico | 424/53 |
| 5,639,445 A | 6/1997 | Curtis et al. | 424/49 |
| 5,702,251 A | 12/1997 | McClintock, II | 433/80 |
| 5,707,235 A | 1/1998 | Knutson | 433/213 |
| 5,711,935 A | 1/1998 | Hill et al. | 424/49 |
| 5,752,826 A | 5/1998 | Andreiko | 433/41 |
| 5,769,633 A | 6/1998 | Jacobs et al. | 433/37 |
| 5,816,802 A | 10/1998 | Montgomery | 433/80 |
| 5,846,058 A | 12/1998 | Fischer | 433/216 |
| 5,851,512 A | 12/1998 | Fischer | 424/49 |
| 5,863,202 A | 1/1999 | Fontenot et al. | 433/215 |
| 5,879,691 A | 3/1999 | Sagel et al. | 429/401 |
| 5,891,453 A | 4/1999 | Sagel et al. | 424/401 |
| 5,894,017 A | 4/1999 | Sagel et al. | 424/401 |
| 5,895,218 A | 4/1999 | Quinn et al. | 433/80 |
| 5,922,307 A | 7/1999 | Montgomery | 424/53 |
| 5,924,863 A | 7/1999 | Jacobs et al. | 433/80 |
| 5,980,249 A | 11/1999 | Fontenot | 433/80 |
| 5,985,249 A | 11/1999 | Fischer | 424/49 |
| 5,989,569 A | 11/1999 | Dirksing et al. | 424/401 |
| 6,045,811 A | 4/2000 | Dirksing et al. | 424/401 |
| 6,080,397 A | 6/2000 | Pfirrmann | |
| 6,089,869 A | 7/2000 | Schwartz | 433/215 |
| 6,096,328 A | 8/2000 | Sagel et al. | 424/401 |
| 6,106,293 A | 8/2000 | Wiesel | 433/215 |
| 6,126,443 A | 10/2000 | Burgio | 433/215 |
| 6,136,297 A | 10/2000 | Sagel et al. | 424/49 |
| 6,142,780 A | 11/2000 | Burgio | 433/80 |
| 6,155,832 A | 12/2000 | Wiesel | 433/215 |
| 6,183,251 B1 | 2/2001 | Fischer | 433/48 |
| 6,197,331 B1 | 3/2001 | Lerner et al. | 424/448 |
| 6,247,930 B1 | 6/2001 | Chiang et al. | 433/80 |
| 6,274,122 B1 | 8/2001 | McLaughlin | 424/53 |
| 6,277,458 B1 | 8/2001 | Dirksing et al. | 424/42.3 |
| 6,280,196 B1 | 8/2001 | Berghash | 433/215 |
| 6,287,120 B1 | 9/2001 | Wiesel | 433/215 |
| 6,309,625 B1 | 10/2001 | Jensen et al. | 424/49 |
| 6,312,671 B1 | 11/2001 | Jensen et al. | 424/53 |
| 6,322,360 B1 | 11/2001 | Burgio | 433/80 |
| 6,331,292 B1 | 12/2001 | Montgomery | 424/53 |
| 6,343,932 B1 | 2/2002 | Wiesel | 433/215 |
| 6,364,665 B1 | 4/2002 | Trettemerp | 433/215 |
| 6,379,147 B1 | 4/2002 | Georgakis et al. | 433/37 |
| 6,419,903 B1 | 7/2002 | Xu et al. | 424/49 |
| 6,419,906 B1 | 7/2002 | Xu et al. | 424/53 |
| 6,435,873 B1 | 8/2002 | Burgio | 433/80 |
| 6,440,396 B1 | 8/2002 | McLaughlin | 424/49 |
| 6,458,380 B1 | 10/2002 | Leaderman | 424/443 |
| 6,461,158 B1 | 10/2002 | Sagel et al. | 433/30 |
| 6,488,914 B1 | 12/2002 | Montgomery | 424/53 |
| 6,497,575 B1 | 12/2002 | Zavitsanos et al. | 433/215 |
| 6,500,408 B1 | 12/2002 | Chen | 424/53 |
| 6,503,486 B1 | 1/2003 | Xu et al. | 424/53 |
| 6,506,053 B1 | 1/2003 | Wiesel | 433/215 |
| 6,514,483 B1 | 2/2003 | Xu et al. | 424/53 |
| 6,514,484 B1 | 2/2003 | Rajaiah et al. | 424/53 |
| 6,551,579 B1 | 4/2003 | Sagel et al. | 424/53 |
| 6,607,382 B1 * | 8/2003 | Kuo et al. | 433/6 |
| 6,638,496 B1 * | 10/2003 | McLaughlin | 424/53 |
| 6,649,147 B1 | 11/2003 | Ye et al. | |
| 6,682,721 B1 | 1/2004 | Kim et al. | |
| 6,689,344 B1 | 2/2004 | Chang et al. | |
| 6,730,316 B1 | 5/2004 | Chen | |
| 2001/0046654 A1 | 11/2001 | Zavitsanos et al. | 433/32 |
| 2002/0006387 A1 | 1/2002 | Sagel et al. | 424/53 |
| 2002/0006388 A1 | 1/2002 | Sagel et al. | 424/53 |
| 2002/0012685 A1 | 1/2002 | Sagel et al. | 424/401 |
| 2002/0018754 A1 | 2/2002 | Sagel et al. | 424/49 |
| 2002/0081555 A1 | 6/2002 | Wiesel | 433/215 |
| 2002/0164292 A1 | 11/2002 | Peterson et al. | 424/53 |
| 2002/0182154 A1 | 12/2002 | McLaughlin | 424/53 |
| 2002/0187111 A1 | 12/2002 | Xu et al. | 424/53 |
| 2002/0187112 A1 | 12/2002 | Xu et al. | 424/53 |
| 2003/0003421 A1 | 1/2003 | Besenheider et al. | 433/215 |
| 2003/0012747 A1 | 1/2003 | Peterson | 424/53 |
| 2003/0036037 A1 | 2/2003 | Zavitsanos et al. | 433/215 |
| 2003/0044631 A1 | 3/2003 | Sagal et al. | 428/548 |
| 2003/0068284 A1 | 4/2003 | Sagel et al. | 424/53 |
| 2003/0068601 A1 | 4/2003 | Zavitsanos et al. | 433/215 |
| 2003/0082114 A1 | 5/2003 | Kim et al. | 424/53 |
| 2003/0133884 A1 | 7/2003 | Chang et al. | 424/53 |
| 2003/0194382 A1 | 10/2003 | Chang et al. | 424/53 |
| 2003/0198606 A1 | 10/2003 | Kim et al. | 424/53 |

* cited by examiner

TRAY-LIKE DENTAL BLEACHING DEVICES HAVING A BARRIER LAYER AND A SUBSTANTIALLY SOLID BLEACHING COMPOSITION

BACKGROUND OF THE INVENTION

1. The Field of the Invention

The present invention is in the field of dental bleaching devices used to bleach a person's teeth. More particularly, the invention relates to dental trays and tray-like barriers loaded with a substantially solid dental bleaching composition that becomes adhesive when moistened (e.g., by a saliva on user's teeth).

2. The Relevant Technology

Virtually all people desire white or whiter teeth. To achieve this goal, people either have veneers placed over their teeth or have their teeth chemically bleached. In the past, patients who desired to have their teeth bleached had to submit to conventional in-office bleaching techniques. The process generally involves: (1) making an alginate impression of the patient's teeth; (2) making a stone cast or model of the impression; (3) vacuum forming a dental tray from the model, usually from a heated sheet of thin ethyl vinyl acetate (EVA) material, and (4) trimming to exclude gingival coverage. This method results in a tray that is soft and flexible, that is customized to very accurately fit over the patient's teeth, and that is therefore very comfortable to wear. However, the process for making a customized tray is time consuming, often taking days or weeks before the customized tray is available to the patient, and the resulting tray can be expensive.

Because of the time and cost associated with customized trays, less time consuming and costly alternatives have been developed. Contrary to marketing campaigns, however, many alternatives have substantial disadvantages, primarily in terms of their effectiveness (or ineffectiveness) in actually bleaching teeth. They also have their own unique issues relating to ease of use, comfort and poor taste (bleaching compositions are, after all, placed directly into a person's mouth).

One alternative to customized dental trays are non-customized trays that approximate the shapes and sizes of a variety of users' dental arches. While non-customized dental trays can be used without the need for a professional customization procedure by a dentist, such trays tend to be more bulky and less comfortable than custom-fitted trays. Dental Trays that can be self-customized (e.g., so-called "boil and bite" trays) are somewhat more comfortable and better-fitting compared to non-custom trays but less comfortable than trays that are customized by a dentist.

Another alternative tooth bleaching method involves painting a bleaching composition directly onto the surfaces of a person's teeth to be bleached. An advantage of this procedure is that it eliminates the need to obtain a customized tray, or even a non-custom tray. The main disadvantage, however, is that the bleaching composition remains directly exposed to the person's saliva and disruptive forces and movements normally found within a person's mouth. The result is that a significant portion of the bleaching composition does not remain on the tooth where bleaching is desired. Instead, some or all of the composition can dissolve away into the person's saliva and/or be transferred to adjacent oral tissues. Because paint-on dental bleaching compositions, like all dental bleaching compositions, contain peroxide-based bleaching agents, irritation to soft oral tissues within the user's mouth and throat is a potential problem when using such compositions.

Yet another alternative tooth bleaching method involves placing a flexible bleaching strip over a user's tooth surfaces. Bleaching strips typically comprise a flexible plastic strip coated with a moist dental bleaching gel on the side of the strip facing the user's teeth. To install the bleaching strip, a portion of the bleaching strip is first placed over the front surfaces of the user's teeth, followed by folding the remainder of the strip around the occlusal edges of the teeth and back against a portion of the lingual surfaces. Like paint-on bleaching compositions, this procedure does not require the user to obtain a customized tray, or even a non-custom tray, into which a bleaching composition must be placed by the user prior to use. An advantage of bleaching strips over paint-on bleaching compositions is that bleaching strips include a barrier that, at least in theory, protects the dental bleaching gel from diffusing into the user's mouth.

In reality, however, because of the generally poor adhesion of bleaching strips to the user's teeth, coupled with their generally flimsy nature, it is often difficult for the user to maintain the bleaching strips in their proper position. Bleaching strips are prone to slip off the teeth through even minimal movement of the user's mouth, jaw or tongue. Indeed, it is recommended that the user not eat, drink, smoke or sleep while wearing the bleaching strip. In practice, it is difficult to talk while maintaining the bleaching strips properly oriented over the teeth to be bleached.

Even if a user successfully maintains the bleaching strip in its proper position during the entire bleaching event, the flowable bleaching gel can diffuse into the person's saliva, potentially causing a poor taste in the user's mouth and possibly discomfort to soft oral and throat tissues. The tendency of the bleaching gel to diffuse into the user's mouth can be accelerated through even minimal shifts of the bleaching strip over the user's teeth, with each shift potentially exposing a new portion of the bleaching gel that remains adhered to the newly exposed surface of the user's teeth. In some cases, the bleaching strip can become so dislodged or mangled that it must be removed by the user and replaced with a fresh bleaching strip to complete the recommended bleaching time. This multiplies the cost and hassle of the bleaching strip method.

In practical terms, the use of bleaching strips can greatly inhibit even the simplest of activities that involve movement of the user's mouth or tongue, such as talking, smiling, making other facial expressions, or even swallowing (which normally occurs subconsciously throughout the day). Indeed, the time when a person's mouth and tongue are prone to move the least is at night while the person is sleeping. Unfortunately, it is recommended that bleaching strips not be used while sleeping, presumably to prevent accidental choking on an inadvertently dislodged bleaching strip. This only confirms the tendency of such bleaching strips to easily dislodge from a user's teeth.

Ultimately, the main impediment to successful bleaching is the failure of users to complete the prescribed bleaching regimen. If the bleaching apparatus is difficult to use, requires numerous repetitions to achieve observable results, or is simply uncomfortable or a hassle to wear, the user may simply give up and abort the bleaching process altogether. Thus, even if significant dental bleaching is possible using a particular bleaching product, it is less likely to occur where the inadequacies of the bleaching apparatus or method causes users to become discouraged before desired results are attained.

In view of the foregoing, there is an ongoing need for improved bleaching apparatus and methods that are simple and easy to use, that more reliably remain in position over the user's teeth, and that result in less diffusion of bleaching composition into a user's oral cavity. Such improvements would be expected to improve or encourage compliance by the user.

BRIEF SUMMARY OF THE PREFERRED EMBODIMENTS

The present invention generally relates to improved dental bleaching devices used to bleach a person's teeth. Briefly summarized, the inventive dental bleaching devices include a moisture-resistant barrier layer, such as a dental tray or tray-like barrier, and a bleaching layer comprising a substantially solid dental bleaching composition that becomes more adhesive to teeth when moistened (e.g., by saliva or water). When placed over a person's teeth, the dental bleaching composition reliably adheres to the teeth, maintaining contact between the teeth to be bleached and a bleaching agent within the bleaching composition. The barrier layer protects the dental bleaching composition from diffusing away from the person's teeth as a result of ambient saliva or moisture found within the person's mouth.

According to one embodiment of the invention, the barrier layer comprises a thin, flexible membrane formed from a moisture-resistant polymer material. Nevertheless, it is within the scope of the invention to provide barrier layers having any desired thickness or rigidity. In a preferred embodiment, the barrier layer comprises a thin layer of a polyolefin or similar moisture-resistant material. The barrier layer may comprise a conventional dental tray, examples of which include both customized and non-custom dental trays. The barrier layer may be as simple as a layer of a moisture resistant material that is sprayed or painted on, applied by dipping, or otherwise applied to an existing bleaching layer comprising a substantially solid dental bleaching composition (e.g., one that is in the form of a dental tray or that otherwise has a desired shape).

In one embodiment, the bleaching layer comprises a substantially solid, coherent dental bleaching composition, as opposed to a liquid, gel, or dry particulate or powdery bleaching composition. As such, the bleaching layer comprises one or more coherent regions or masses of a dental bleaching composition that do not readily run or flow. Providing a substantially solid and coherent bleaching layer better maintains the bleaching composition between the barrier layer and the teeth being bleached and helps prevent diffusion into the surrounding oral cavity. This, in turn, promotes better tooth whitening and reduces irritation to surrounding oral tissues and/or at least some of the bad taste normally associated with dental bleaching.

The substantially solid dental bleaching compositions according to the invention include at least one dental bleaching agent and at least one tooth adhesion agent. Preferred dental bleaching agents include solid complexes of hydrogen peroxide. Non-limiting examples of dental bleaching agents that are a solid complex of hydrogen peroxide are carbamide peroxide and sodium perborate, although it is within the scope of the invention to use other dental bleaching agents known in the art.

In one embodiment, the tooth adhesion agent advantageously remains substantially non-adhesive when the dental bleaching composition is in a dry or substantially solid condition but becomes adhesive to teeth when the dental bleaching composition is moistened with, e.g., water or saliva. A non-limiting example of a suitable tooth adhesion agent is polyvinyl pyrrolidone (PVP), although it is within the scope of the invention to use other tooth adhesion agents known in the art.

The dental bleaching composition may include other components as desired to yield a final composition having desired properties. Examples of other components include, but are not limited to, plasticizers and humectants (e.g., glycerin, sorbitol, and polyethylene glycol), volatile solvents (e.g., water and alcohols), stabilizing agents (e.g., EDTA), neutralizing agents, thickening agents (e.g., fumed silica), desensitizing agents (e.g., potassium nitrate), remineralizing agents (e.g., sodium fluoride or other fluoride salts), antimicrobial agents (e.g., chlorhexidine), antiplaque agents, anti-tartar agents, other medicaments, flavorants, sweeteners, and the like.

According to one embodiment, the dental bleaching composition is made by first forming a flowable liquid or gel composition that is later subsequently dried to form a substantially solid bleaching layer. This may be performed by heating or otherwise causing one or more volatile solvents to be driven off by evaporation, thus leaving behind a substantially solid bleaching composition. The drying process may be performed before or after the bleaching composition is placed into contact with the barrier layer.

According to one embodiment, dental bleaching devices can be made by spreading a flowable dental bleaching composition onto the surface of a large or continuous polymeric sheet. The polymeric sheet and bleaching composition are then heated, such as in a forced air oven, to drive off a substantial portion of the water or other solvent that was used to form the flowable dental bleaching composition in order to yield a substantially solid layer of bleaching composition. Thereafter, individual tray-like dental bleaching devices can be molded or stamped from the large or continuous polymeric sheet coated with the substantially solid layer of bleaching composition and then separated as individual bleaching devices suitable for placement over a person's teeth.

Alternatively, a flowable or substantially solid dental bleaching composition can be molded or shaped into a desired tray-like configuration comprising the bleaching layer. Thereafter, a barrier layer can be attached or applied to an outer surface of the bleaching layer. In yet another embodiment, a dental tray can be coated with a flowable dental bleaching composition, such as by painting or spreading, and then heated or allowed to dry at room temperature so that the bleaching composition becomes substantially solid.

The size and shape of dental bleaching devices according to the invention can be tailored to more readily fit a person's upper or lower dental arch. They may also be tailored to fit person's having differently sized or shaped dental arches. The dental bleaching devices are advantageously designed so as to substantially cover the front and lingual surfaces of the teeth to bleached. Bleaching both surfaces yields more esthetically appealing teeth. Moreover, bleaching both the front and lingual surfaces helps in bleaching the interproximal spaces between adjacent teeth. The dental bleaching devices are advantageously flexible and adhesive so as to readily conform to a wide variety of differently-sized teeth and dental arches.

The dental bleaching devices according to the invention are preferably in the shape of a dental tray having a front side wall, a rear side wall, and a trough between the front and rear side walls. Having the shape of a dental tray facilitates placement of the dental bleaching device over a person's teeth by minimizing the amount of manipulation that is necessary to obtain a good fit between the device and the person's teeth. Dental bleaching devices that are in the shape of a dental tray and that have a substantially solid bleaching layer that becomes more adhesive when moistened with water or saliva are easier to install over a person's teeth than flat bleaching strips. In addition, the inventive dental bleaching devices are designed to more reliably remain in place over the person's teeth compared to conventional bleaching strips. The result is more effective tooth bleaching and better patient compliance.

According to one embodiment, the dental bleaching device has a horseshoe shape and a U-shaped trough like a conventional bleaching tray. In another embodiment, the bleaching device has an L-shaped profile or "trough". It will be appreciated, however, that dental bleaching devices according to the invention can have any longitudinal profile or shape (e.g., they can be straight or have any desired degree of longitudinal curvature from one end of the device to the other). The trough may have any desired cross-sectional shape (e.g., the trough can be V-shaped, trapezoidal, rectangular, or other geometric shape).

To facilitate the ability of a dental treatment device to conform to the various shapes and sizes among dental arches, the dental treatment device may include mechanical features such as a notch within the front side wall, preferably within an edge near the center of the front side wall, and/or a notch within the rear side wall, preferably within an edge near the center of the rear side wall. Notches allow the tray-like bleaching device to more easily conform to differently-sized dental arches. In this way, the dental bleaching device can be designed so as to be "one-size fits all".

The dental bleaching devices according to the invention can be designed to be worn for any desired time period. Increasing the concentration of dental bleaching agent generally reduces the required bleaching time. Nevertheless, due to the extremely comfortable fit and reliable adhesion between the inventive dental bleaching devices and the person's teeth, it is possible to wear such devices for extended periods of time in order to ensure even and thorough bleaching. Dental bleaching devices according to the invention can be designed to be worn while, e.g., talking, sleeping, eating, drinking, smiling, frowning, grimacing, yawning, coughing, smoking, or making virtually any facial expression or mouth contortion. This greatly decreases their intrusiveness into everyday activities compared to conventional bleaching strips, which do not reliably adhere to teeth, or intrusive bleaching devices such as large, bulky bleaching dental appliances.

The dental bleaching devices can be designed to be worn for as little as a few minutes or as long as several hours. By way of example, not limitation, a typical bleaching session of fast duration may last from about 10 to about 30 minutes. A bleaching session of intermediate duration may last from about 30 minutes to about 2 hours. A bleaching session of long duration, including professional bleaching or overnight bleaching while a person is sleeping, may last from about 2 hours to about 12 hours. Bleaching sessions may be repeated as many times as are needed to obtain a desired degree of whitening. In some cases, a clinical whitening effect has been observed after only 1–3 whitening sessions. A typical bleaching regimen will preferably include 1–20 bleaching sessions, more preferably 2–15 bleaching sessions, and most preferably 3–10 bleaching sessions.

For convenience of use, multiple dental bleaching devices may be packaged together and sold as a kit. In one embodiment, the number of dental bleaching devices provided with each kit can equal the number of sessions that represent a prescribed bleaching regimen. To efficiently utilize the space within a kit package, multiple dental bleaching devices can be stacked and interested together. The dental bleaching devices can be sealed collectively or individually as desired. They may contain a removable protective layer on their interior surfaces to protect the bleaching layer from contamination or moisture, both of which can possibly cause premature decomposition of the peroxide bleaching agent. It is within the scope of the invention to provide barrier layers and bleaching composition that are initially separate and that are brought together by the end user. The bleaching composition may be a dry or substantially solid insert or it may be a liquid or gel that is applied to the barrier and allowed to dry prior to placement of the finished dental treatment device over the person's teeth.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction and Definitions

Figure 1:
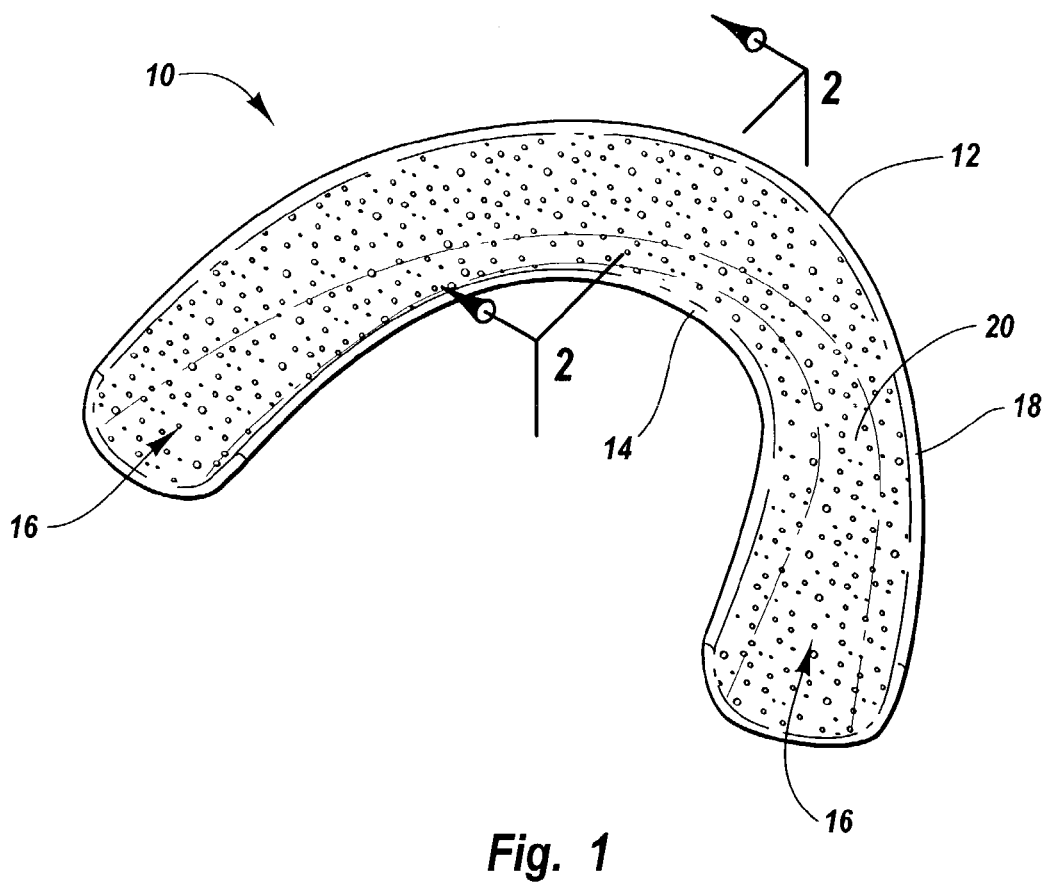
FIG. 1 is a perspective view of an exemplary dental bleaching device according to the invention in the shape of a dental tray comprising a barrier layer and a substantially solid dental bleaching composition.

The present invention generally relates to improved dental bleaching devices used to bleach a person's teeth. The inventive dental bleaching devices include a moisture-resistant barrier layer and a substantially solid dental bleaching composition that becomes more adhesive to teeth when moistened with water or saliva. When placed over a person's teeth, the dental bleaching composition reliably adheres to the teeth, maintaining contact between the teeth to be bleached and a bleaching agent within the bleaching composition. The barrier layer protects the dental bleaching composition from diffusing away from the person's teeth as a result of ambient saliva or moisture found within the person's mouth.

The inventive bleaching devices are more adhesive to teeth than conventional bleaching strips. The inventive dental bleaching devices are also less intrusive than bulky, over-the-counter, non-custom or boil and bite dental trays. In some ways they are as reliable, or even more reliable than custom-fitted dental trays in maintaining the dental bleaching composition against a person's teeth. In some cases, they are also as comfortable, or even more comfortable, than custom-fitted trays.

The term "barrier layer", as used herein, refers to one or more layers of a moisture-resistant material that protects the bleaching layer from ambient moisture and saliva found within a person's mouth when the dental bleaching device is placed over the person's teeth. The barrier layer may also serve to protect the bleaching layer from moisture or other contaminants during storage and prior to use. The barrier layer may be in any desired form including, but not limited to, a sheet laminated to a surface of the bleaching layer, a coating applied to a pre-formed bleaching layer, or a dental treatment tray.

The term "bleaching layer", as used herein, refers to one or more layers of a dental bleaching composition that has been formulated or processed so as to be substantially solid, coherent, and non-flowable. The bleaching layer may comprise a single continuous region or layer adjacent to the barrier layer, or it may comprise a plurality of discontinuous regions or layers spaced-apart by random or predetermined intervals.

The term "substantially solid", as used herein, refers to a dental bleaching composition or bleaching layer that is in a solid or semi-solid condition. In one aspect, a "substantially solid" bleaching composition or layer can be characterized as a continuous or cohesive mass that does not readily flow or separate when subjected to gravitational forces and which cannot be readily expressed through a syringe outlet or other similarly-sized opening or orifice. Thus, the term "substantially solid" excludes runny bleaching liquids, viscous bleaching liquids, and even thick bleaching gels that are able to flow when subjected to gravity and/or which can be readily expressed through a syringe outlet or other similarly-sized opening or orifice. The term "substantially solid", when used in the context of a bleaching composition or layer, also excludes dry particulate bleaching compositions or powders because dry particulates and powders readily flow when subjected to gravity and/or are readily separated (i.e., the particles as a whole have little or no internal cohesion).

One characteristic of "substantially solid" bleaching compositions or layers according to the invention is that they become more adhesive when an exposed surface thereof is moistened with, e.g., saliva or water. When moistened, the surface of the bleaching composition or layer turns into a sticky material that is able to more strongly adhere to teeth compared to a substantially solid bleaching composition or layer that has not been moistened. The composition at the surface may become a viscous liquid, paste or gel, at least temporarily, depending on the amount of moisture that is applied to the surface of the "substantially solid" bleaching composition or layer. Nevertheless, the consistency of the moistened surface can remain "substantially solid" depending on the degree of initial moistening, or it can stiffen and even revert back to being "substantially solid" as the initial quantity of surface moisture diffuses into a remaining portion of the "substantially solid" bleaching composition or layer over time (e.g., during a bleaching procedure in which the bleaching layer or composition is protected from saliva and ambient moisture in a person's mouth by a water-proof barrier layer).

The term "dental tray", as used herein, refers to any article of manufacture or device having a tray-like shape so as to facilitate placement of the device over at least a portion of a person's dental arch. A "dental tray" or "tray-like" device includes a front side wall configured to engage front surfaces of a person's teeth when in use, a rear side wall extending laterally from the front side wall, either abruptly by one or more distinct angles or non-abruptly by a curved transition, configured to engage lingual surfaces of the person's teeth, and a trough between said front and rear side walls. A "dental tray" may be configured so that a portion of the front side wall, rear side wall, or a transition portion thereof engages the incisal or occlusal edges of the person's teeth when in use. The dental tray may be curved or straight in a longitudinal dimension.

The term "trough", as used herein, refers to the region that is at least partially bounded by the front side wall, the rear side wall, and a plane or imaginary curved dome extending from an upper edge of the front side wall and an upper edge of the rear side wall. Thus, a "trough" can theoretically exist whenever the front and rear side walls have a space therebetween and are laterally offset by an angle of less than 180°. In practice, the front and rear side walls will be offset by an angle that is preferably less than about 150°, more preferably less than about 120°, and most preferably less than about 90°.

In the case of a trough having a U-shaped or rectangular cross section, at least a portion of the front and rear side walls may be substantially parallel (i.e., be offset by an angle of approximately 0°). In the case of a trough having a V-shaped or trapezoidal cross section, at least a portion of the front and rear side walls may be offset by an acute angle (i.e., by an angle between 0–90°). In the case of a trough having an L-shaped cross section, at least a portion of the front and rear side walls will be offset by an angle centered around approximately 90° (e.g., by an angle in a range of about 70° to about 110°). Thus, a trough having an L-shaped cross section can be a subset or slight variation of a trough having a V-shaped cross section.

The terms "longitudinal", "longitudinal dimension" and "longitudinal profile", as used herein when used to refer to a dental tray or dental treatment device, shall refer to the lengthwise dimension of the tray or device. The tray or device may be straight in the "longitudinal dimension" or it may be horseshoe-shaped or otherwise "longitudinally curved" in the longitudinal dimension so as to approximate the curvature of a person's dental arch, or at least facilitate placement of the tray or device over the dental arch.

The term "molecular weight", as used herein, refers to number average molecular expressed in Daltons unless otherwise specified.

II. Dental Bleaching Devices

Inventive dental bleaching devices according to the invention include a bleaching layer that becomes more adhesive to teeth when moistened by, e.g., saliva or water, and a moisture-resistant barrier layer that protects the bleaching layer from ambient moisture within a person's mouth during use. Following are preferred examples of materials and characteristics of barrier layers and bleaching layers according to the invention.

A. Barrier Layers

According to one embodiment of the invention, the barrier layer comprises a thin, flexible membrane formed from a moisture-resistant polymer material. In a preferred embodiment, the barrier layer comprises a thin, flexible layer of a polyolefin or similarly moisture-resistant material, such as wax, metal foil, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes or polyesteramides. Such materials may be provides in the form of large, flat, flexible sheets to which the bleaching layer is applied. Alternatively, such sheets may be applied or attached to an existing bleaching layer comprising a substantially solid dental bleaching composition.

Notwithstanding the foregoing, it is within the scope of the invention to provide barrier layers having any desired material, thickness or rigidity so long as the barrier layer provides at least some moisture protection relative to the bleaching layer. The barrier layer may comprise a conventional dental tray, examples of which include both customized and non-custom dental trays. The barrier layer may be as simple as a layer of a moisture resistant material that is sprayed or painted on, applied by dipping, or otherwise applied to an existing bleaching layer (e.g., one that is in the form of a dental tray or that otherwise has a desired shape).

Examples of suitable polyolefins for use in making the barrier layer include, but are not limited to, polyethylene (PE), high density polyethylene (HDPE), low density polyethylene (LDPE), ultra low density polyethylene (ULDPE), polypropylene, and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. Plasticizers, flow additives, and fillers known in the art can be used as desired to modify the properties of any of the foregoing polymers used to form the barrier layer.

As will be discussed below, some dental bleaching compositions will be more adhesive to polymer materials comprising the barrier layer than others, often depending on the tooth adhesion agent that is used. It has been found that, as between polyethylene, paraffin and polyethylene terephthalate, substantially solid dental bleaching compositions tend to adhere more strongly to polyethylene terephthalate, particularly MYLAR.

It is also within the scope of the invention to utilize barrier layers that are formed onto a surface of a previously formed bleaching layer, such by adhering a sheet or tray-like barrier layer to the bleaching layer. Alternatively, the barrier layer may itself be initially flowable and later hardened, such as a lacquer that contains a barrier material (e.g., a cellulosic ether, cellulose acetate, wax, plastic, polyvinyl acetate, polyvinyl alcohol, or shellac) dissolved in one or more solvents that are later removed; a chemical or light-cure material (e.g., a methacrylate or acrylate resin); or a thermoplastic melt (e.g., any thermoplastic resin). Examples of useful cellulosic ethers that can be used to form a barrier layer include, but are not limited to, ethyl cellulose, propyl cellulose, isopropyl cellulose, butyl cellulose, t-butyl cellulose, and the like.

B. Bleaching Layers

Prior to being moistened in preparation for or during use, bleaching layers within dental bleaching devices according to the invention preferably comprise a substantially solid and coherent dental bleaching composition, as opposed to a liquid, a flowable gel, or a dry powder or particulate bleaching composition. The bleaching layer may comprise a single coherent mass or region, or it may comprise a plurality of coherent masses or regions of a substantially solid dental bleaching composition. Providing a substantially solid and coherent bleaching layer better maintains the bleaching composition between the barrier layer and the teeth being bleached instead of diffusing into the surrounding oral cavity, as compared to conventional bleaching gels that are loaded into customized or non-customized dental trays or that are applied using bleaching strips. This, in turn, promotes better tooth whitening and reduces irritation to surrounding oral tissues and/or at least some of the bad taste normally associated with dental bleaching.

Substantially solid dental bleaching compositions that comprise the bleaching layer according to the invention include at least one bleaching agent and at least one tooth adhesion agent. In a preferred embodiment, the bleaching agent is dispersed within a substantially solid matrix comprising the tooth adhesion agent. Following are preferred bleaching agents and tooth adhesion agents.

1. Bleaching Agents

A common dental bleaching agent that is known to bleach teeth and that has been found to be safe for oral use is hydrogen peroxide. However, hydrogen peroxide does not itself exist free in nature, but only as an aqueous solution or as a complex. Preferred dental bleaching agents comprise complexes of hydrogen peroxide because they are more stable than aqueous hydrogen peroxide, which tends to be unstable when heated, especially when water is removed by evaporation.

Non-limiting examples of complexed hydrogen peroxide include carbamide peroxide and metal perborates. Other bleaching agents that can be used to bleach teeth include, but are not limited to, metal percarbonates, peroxides, chlorites, and hypochlorites, peroxy acids, and peroxy acid salts.

Bleaching agents within the substantially solid dental bleaching compositions according to the invention can have any desired concentration, e.g., between 1–90% by weight of the substantially solid dental bleaching composition. The concentration of the dental bleaching agent can be adjusted depending on the intended treatment time for each bleaching session. In general, the shorter the treatment time, the more bleaching agent will be added to accelerate dental bleaching so as to effect bleaching in a shorter time period.

The one or more bleaching agents are preferably included in an amount in a range of about 5% to about 80% by weight of the substantially solid dental bleaching composition, more preferably in a range of about 10% to about 60% by weight of the substantially solid dental bleaching composition, and most preferably in a range of about 20% to about 50% by weight of the substantially solid dental bleaching composition.

2. Tooth Adhesion Agents

The tooth adhesion agent may comprise any known tackifying agent that is substantially non-adhesive, or less adhesive, when the dental bleaching composition is substantially solid but which becomes more adhesive to teeth when the dental bleaching composition is moistened with, e.g., water or saliva. A presently preferred tooth adhesion agent is polyvinyl pyrrolidone (PVP). PVP polymers have been found to provide excellent adhesion to polymer barrier layers made from PE, PET and paraffin, to be substantially non-adhesive adhesive when the dental bleaching composition is dry to the touch, and to have superior adhesion to teeth when a surface of a substantially solid dental bleaching composition is moistened with saliva or water.

Non-limiting examples of polyvinyl pyrrolidone polymers that have been used in formulating bleaching compositions and layers according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million. Because PVP polymers having widely varying molecular weights have been found to provide similar adhesion and wetting properties, it is believed that PVP polymers of any molecular weight, at least those having a molecular weight between 50,000 and 1.3 million, will be useful in formulating substantially solid bleaching compositions or layers according to the invention.

Other tooth adhesion agents that may be used in addition to, or instead of, PVP within the scope of the invention include, but are not limited to, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like.

Although polyethylene oxide polymers comprises a less preferred tooth adhesion agent, it has been found that a polyethylene oxide polymer having a molecular weight of 1 million provides better adhesion to barrier layers such as MYLAR than a polyethylene oxide polymer having a molecular weight of 100,000.

The one or more tooth adhesion agents are preferably included in an amount in a range of about 10% to about 90% by weight of the substantially solid dental bleaching composition (exclusive of any bound water or other solvent), more preferably in a range of about 20% to about 80% by weight of the substantially solid dental bleaching composition, and most preferably in a range of about 40% to about 75% by weight of the substantially solid dental bleaching composition.

3. Other Components

The dental bleaching composition may include other components as desired to yield a final composition having desired properties. Examples of other components include, but are not limited to, plasticizers and humectants (e.g., glycerin, sorbitol, and polyethylene glycol), volatile solvents (e.g., water and alcohols, such as ethanol), stabilizing agents (e.g., EDTA), neutralizing agents (e.g., sodium hydroxide), thickening agents (e.g., fumed silica), desensitizing agents (e.g., potassium nitrate, other potassium salts, citric acid, citrates, and sodium fluoride), remineralizing agents (e.g., sodium fluoride, stannous fluoride, sodium monofluorophosphate, and other fluoride salts), antimicrobial agents (e.g., chlorhexidine, troclosan, and tetracycline), antiplaque agents, anti-tartar agents (e.g., pyrophosphates salts), other medicaments, flavorants, sweeteners, and the like.

When water is used as a solvent when manufacturing bleaching layers according to the invention and then driven off by evaporation to yield a substantially solid dental bleaching composition, it is postulated that a significant amount of water remains bound or associated with the hydrophilic components within the dental bleaching composition, including the dental bleaching agent, the tooth adhesion agent, and any polyols added as humectants. Although the amount of residual water has not yet been determined, it is believed that approximately 10% of the water added initially remains after the initially flowable dental bleaching composition is dried sufficiently to yield a substantially solid bleaching composition.

C. Characteristics of Dental Bleaching Devices

The dental bleaching devices according to the invention are preferably in the shape of a dental tray having a front side wall, a rear side wall, and a trough between the front and rear side walls. Having the shape of a dental tray facilitates placement of the dental bleaching device over a person's teeth by reducing the amount of manipulation that is necessary to obtain a good fit between the device and the person's teeth.

Dental bleaching devices that are in the shape of a dental tray and that have a substantially solid bleaching layer that becomes more adhesive when moistened with water or saliva are easier to install over a person's teeth compared bleaching strips or patches, which are initially flat and which must be manipulated so as to wrap the initially flat strip or patch around the occlusal or incisal edges of the teeth in order to cover the front and lingual tooth surfaces. In addition, the inventive dental bleaching devices are designed to more reliably adhere and remain in place over the person's teeth compared to conventional bleaching strips, which employ a dental bleaching gel that is already flowable prior to placing the bleaching strip over a person's teeth to be bleached. The result is more effective tooth bleaching and better patient compliance. In contrast to conventional bleaching strips, which are not recommended for use while a person eats, drinks, smokes or sleeps, dental bleaching devices according to the invention can be designed so as to be worn while talking, sleeping, eating, drinking, smiling, frowning, grimacing, yawning, coughing, smoking, or making virtually any facial expression or mouth contortion.

Figure 2:
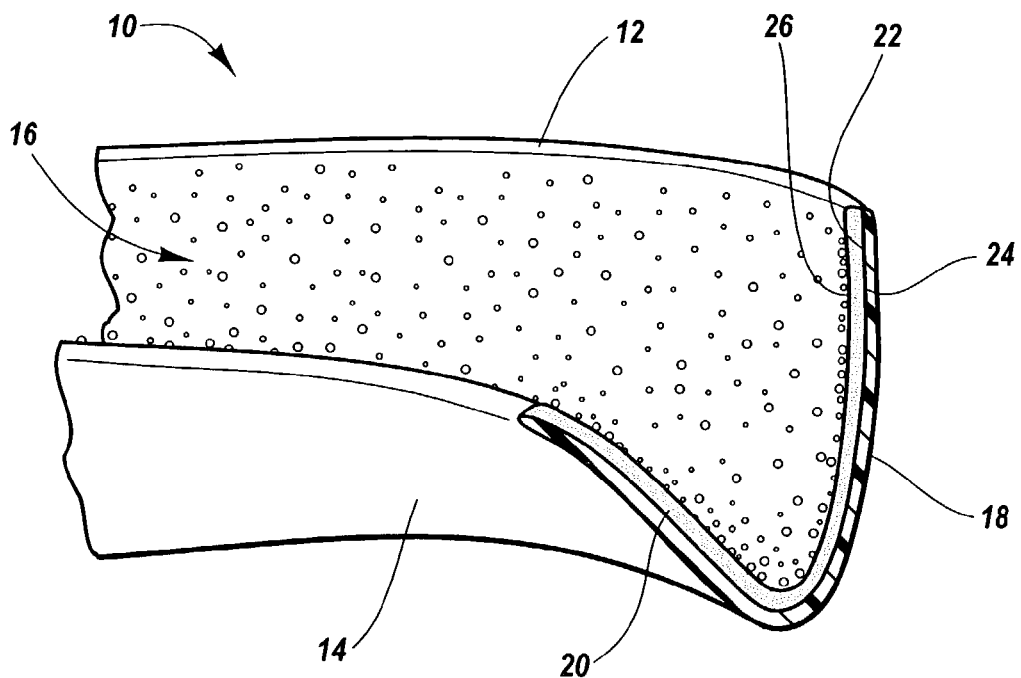
FIG. 2 is a cross-sectional view of the dental bleaching device depicted in FIG. 1.

According to one currently preferred embodiment, the dental bleaching device has a horseshoe shaped longitudinal profile and has a trough with a U-shaped cross section, much like a conventional bleaching tray. Such a device is depicted in FIGS. 1 and 2. FIG. 1 is a perspective view of a dental bleaching device 10 having a front side wall 12 and a rear side wall 14 that together have a generally horseshoe shape in a longitudinal dimension and that define a trough 16 having a generally U-shaped cross section. The U-shaped cross section of the trough is seen even more clearly in FIG. 2.

The dental bleaching device 10 further includes a barrier layer 18, preferably comprising a moisture-resistant material, and a coherent bleaching layer 20, preferably comprising a substantially solid dental bleaching composition. As best seen in FIG. 2, the bleaching layer 20 includes an exterior surface 22 disposed adjacent to an interior surface 24 of the barrier layer 18 and an interior bleaching surface 26 designed to directly contact a person's teeth when the dental bleaching device 10 is in use.

Figure 3:
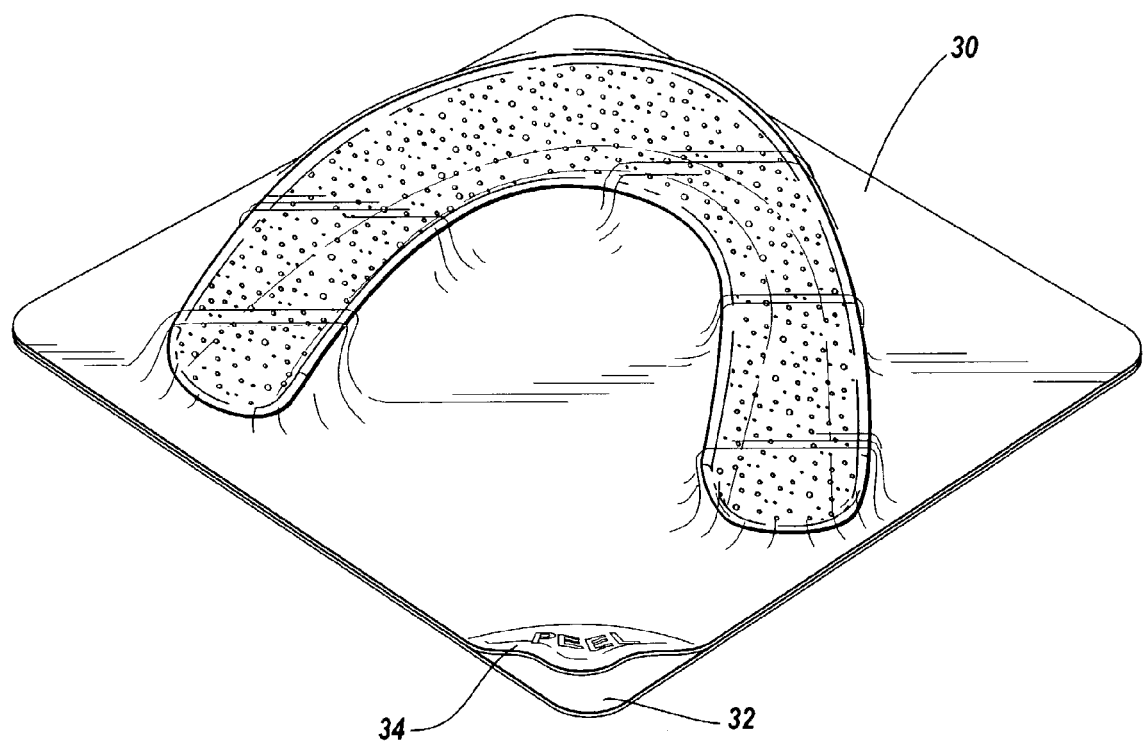
FIG. 3 illustrates the dental bleaching device of FIG. 1 contained within a sealed protective package having a peelable cover.

In order to protect a dental bleaching device according to the invention from contaminants during storage and prior to use, the dental bleaching device can be packaged within a sealed container or package. As illustrated in FIG. 3, the dental bleaching device 10 can be sealed within a protective package 30 that includes a rigid support layer 32 and a peelable cover 34. When it is desired to use the dental bleaching device 10, the peelable cover 34 is removed and the bleaching device 10 is removed or separated from the support layer 32. In addition to, or instead of, the protective package 30, the dental bleaching device 10 may alternatively include a removable protective layer (not shown) that is temporarily placed adjacent to the interior bleaching surface 26 of the bleaching layer 20. When it is desired to use the dental bleaching device 10, the removable protective layer is removed so as to expose the interior bleaching surface 26.

Figure 4:
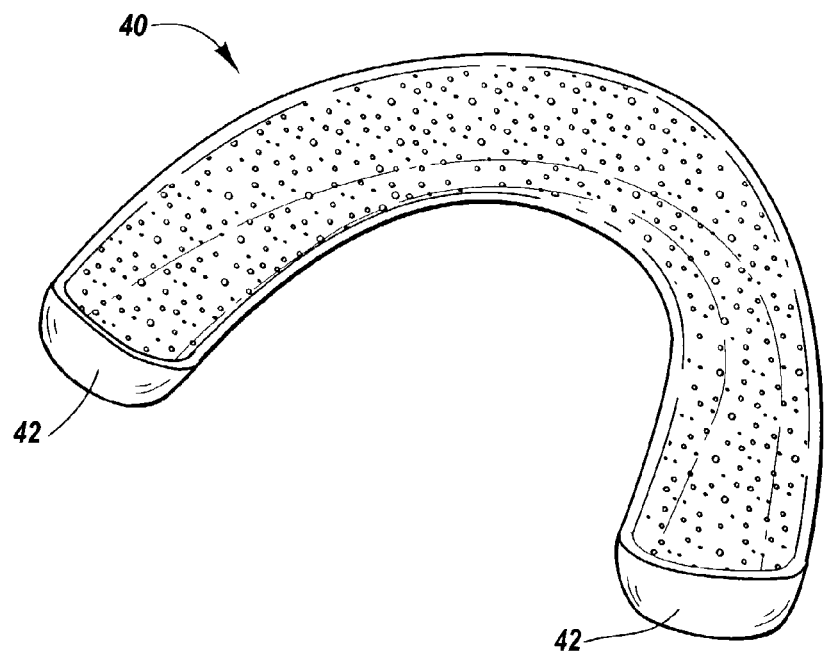
FIG. 4 is a perspective view of an exemplary dental bleaching device that is similar to the bleaching device depicted in FIG. 1, but that further includes a terminal side wall on each longitudinal end.

FIG. 4 illustrates a dental bleaching device 40 that is a variation of the U-shaped dental bleaching device 10 of FIG. 1. The main difference is that each longitudinal end 42 of the dental bleaching device 40 is raised so as to at least partially enclose the last tooth on each side of a person's dental arch when the bleaching device 40 is in use.

Figure 5:
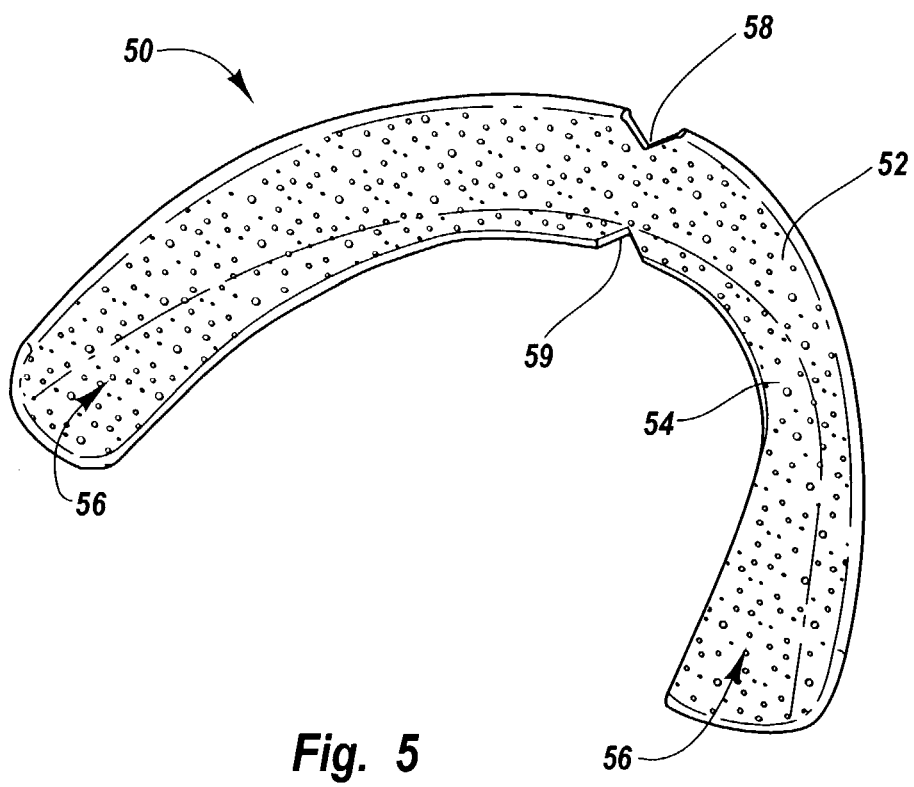
FIG. 5 is a perspective view of an exemplary dental bleaching device having an L-shaped trough and a curved longitudinal profile.

FIG. 5 illustrates an alternative embodiment of a dental bleaching device 50 according to the invention that is L-shaped. More particularly, the dental bleaching device 50 includes a front side wall 52 and a rear side wall 54 extending laterally from the front side wall 52 so as to form a trough 56 having an approximate L-shaped cross section. The L-shaped bleaching device 50 of FIG. 4 is somewhat easier to initially place over a person's dental arch compared to the U-shaped bleaching devices of FIGS. 1–4. This is due to the approximately planar orientation of the rear side wall 54 relative to the occlusal or incisal edges of a person's teeth when the front side wall 52 of the dental bleaching device 50 is initially placed and adhered against the front surfaces of a person's teeth. On the other hand, more manipulation of an L-shaped device is generally required to form and adhere the rear side wall 54 against the lingual surfaces of the person's teeth as a result of the greater initial offset angle between the front side wall 52 and rear side wall 54. However, the ability of dental bleaching devices according to the invention to adhere to tooth surfaces almost immediately, or within a few seconds, after the substantially solid bleaching composition is wetted facilitates the process of conforming the front side wall 52 and rear side wall 54 to the person's tooth surfaces.

In the case of the dental bleaching device 50 having an L-shaped cross section, it may be more correct to say that the rear side wall 54 extending laterally from the front side wall 52 is really a bottom wall rather than a rear side wall. Nevertheless, because this erstwhile "bottom wall" of an L-shaped bleaching device is folded back against the lingual tooth surfaces during use, it can be readily seen that a bleaching device having an L-shaped trough is merely a variation of a device having a V-shaped trough. Thus, for purposes of this disclosure and the appended claims, the side wall 54 shall constitute, and fall within the definition of, a "rear side wall".

To facilitate the ability of a dental treatment device to conform to the varying shapes and sizes among dental arches, the dental treatment device may include mechanical features such as one or more notches within the front or rear side walls. As shown in FIG. 5, the dental bleaching tray 50 includes a notch 58 in an outer edge near the center of the front side wall 52 and a notch 59 in an outer edge near the center of the rear side wall 54. Notches 58 and 59 allow the tray-like bleaching device to more easily spread open or compress when being conformed to differently-sized dental arches. In this way, the dental bleaching device 50 can more easily be a "one-size fits all" device.

Figure 6:
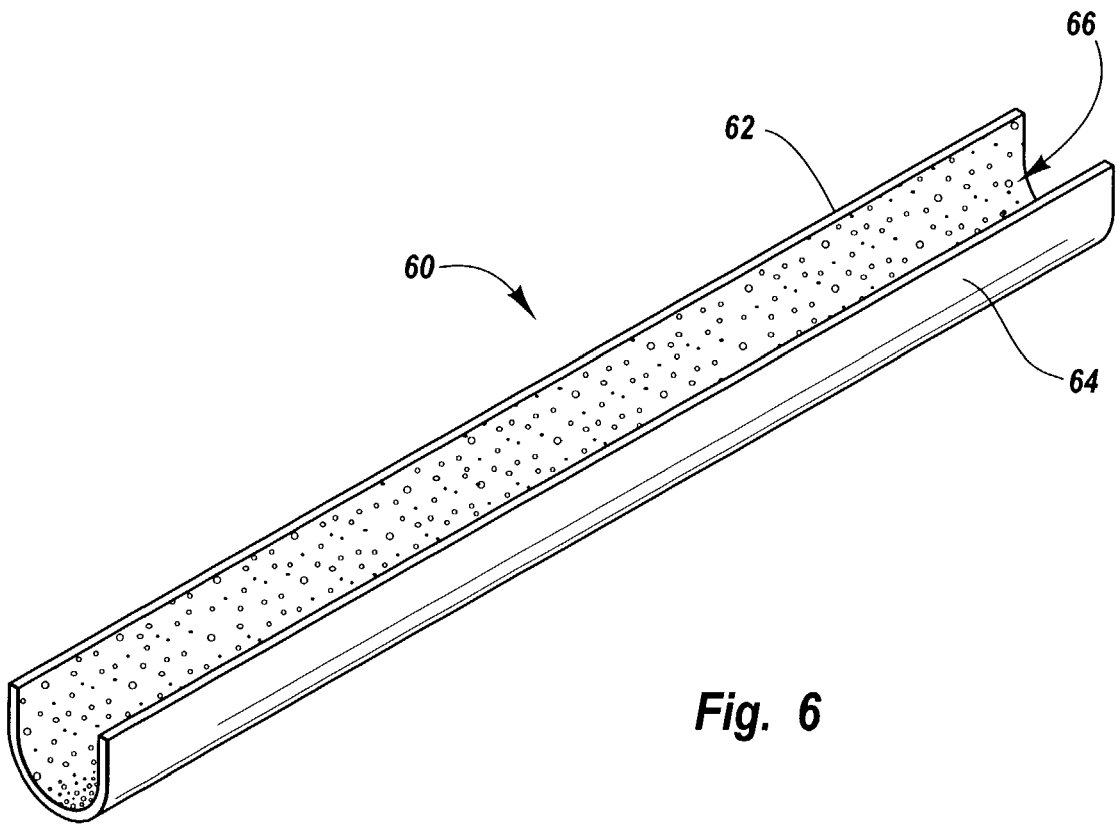
FIG. 6 is a perspective view of an exemplary dental bleaching device having a U-shaped trough and a substantially straight longitudinal profile.

FIG. 6 depicts an alternative embodiment of a dental bleaching device 60 according to the invention, which includes a front side wall 62 and a rear side wall 64 that define a U-shaped trough 66. Instead of being horseshoe shaped like the dental bleaching device 10 of FIGS. 1–5, or otherwise having a curved longitudinal profile, the dental bleaching device 60 of FIG. 6 has a substantially straight or linear longitudinal profile.

Figure 7:
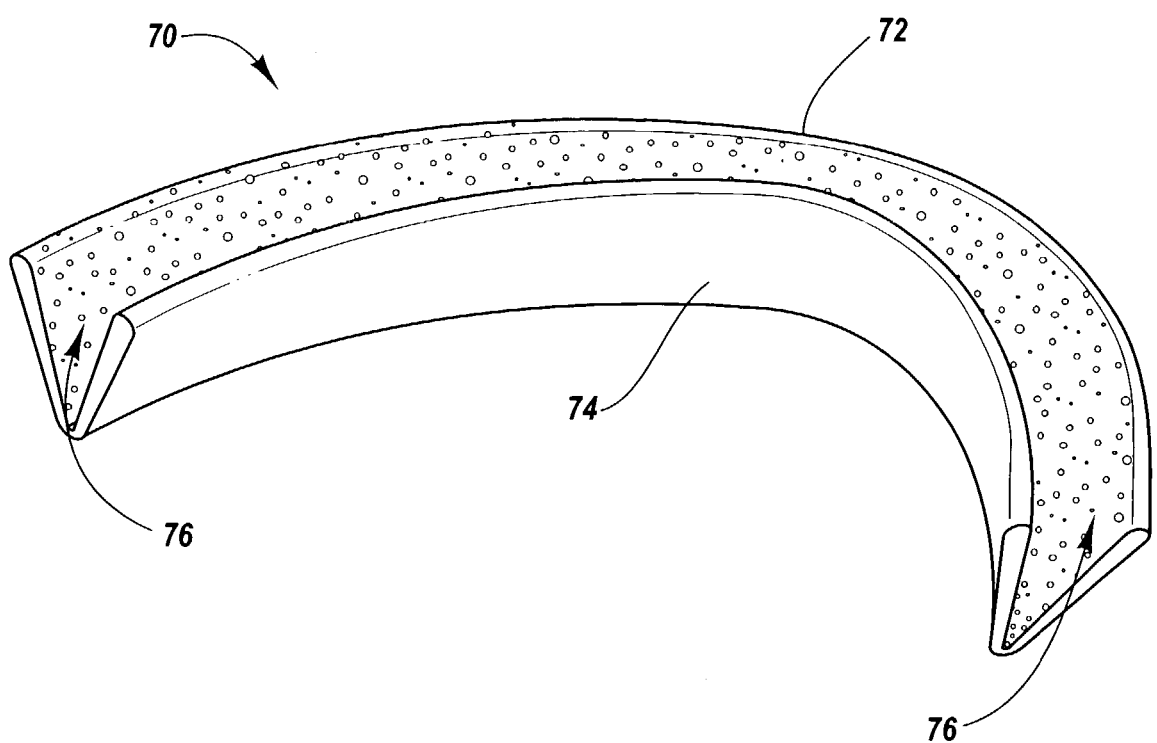
FIG. 7 is a perspective view of an exemplary dental bleaching device having a V-shaped trough and a curved longitudinal profile.

FIG. 7 depicts yet another alternative embodiment of a dental bleaching device 70 according to the invention. The dental bleaching device 70 includes a front side wall 72 and a rear side wall 74 that define a V-shaped trough 76 and a curved longitudinal profile. The main difference between the V-shaped bleaching device 70 of FIG. 7 and the L-shaped bleaching device 50 of FIG. 5 is the angle at which the front and rear side walls are laterally offset from each other.

Notwithstanding the foregoing examples, it will be appreciated that dental bleaching devices according to the invention can have any longitudinal shape (e.g., they can have a straight or curved longitudinal profile from one end to the other). The front and rear side walls may define a trough of any desired cross-sectional shape (e.g., the trough can be trapezoidal, rectangular, or any other desired geometric shape).

The size and shape of dental bleaching devices according to the invention can be tailored to more readily fit either a person's upper dental arch or lower dental arch. They an be sized so as to bleach all or merely a subset of a person's teeth. The dental bleaching devices may be sufficiently adhesive and flexible so as to readily conform to a wide variety of differently-sized teeth and dental arches. The dental bleaching devices are advantageously designed so as to substantially cover the front and lingual surfaces of the teeth to bleached. Bleaching both surfaces yields more esthetically appealing teeth, although it is certainly within the scope of the invention to bleach more of one surface than another. Bleaching the front and lingual surfaces helps to bleach the interproximal spaces between adjacent teeth.

In general, the thickness of the barrier layer and/or the bleaching layer can be adjusted to yield a dental bleaching device having a desired strength and flexibility. In order for the barrier layer to remain flexible so as to conform to a person's teeth, the barrier layer will generally have a thickness ranging from about 0.025 mm to about 1.5 mm. The bleaching layer will generally have a thickness ranging from about 0.1 mm to about 3 mm. The thickness of the bleaching layer can also be selected depending on the intended duration of each bleaching session. In generally, increasing the thickness of the bleaching layer will provide a longer or more sustained release of active dental bleaching agent. By way of example, for short wear times, the bleaching layer will preferably have a thickness ranging from about 0.1 mm to about 0.5 mm. For intermediate wear times, the bleaching layer will preferably have a thickness ranging from about 0.5 mm to about 2 mm. For professional use and for overnight bleaching, the bleaching layer will preferably have a thickness ranging from about 2 mm to about 3 mm.

III. Methods of Making Dental Bleaching Devices

According to one embodiment, the dental bleaching composition is made by first forming a flowable bleaching composition that is later dried to form a substantially solid bleaching layer. This may be performed by heating or otherwise causing one or more volatile solvents to be driven off by evaporation, thus leaving behind a substantially solid bleaching composition. The drying process may be performed before or after the bleaching composition is placed into contact with the barrier layer.

According to one embodiment, dental bleaching devices can be made by spreading a flowable dental bleaching composition onto the surface of a large or continuous polymeric sheet. The polymeric sheet and bleaching composition are then placed into a forced air oven or other appropriate desiccation device in order to heat and drive off a substantial portion of the water or other solvent used to form the flowable dental bleaching composition. Removal of the volatile solvent yields a bleaching layer comprising a substantially solid bleaching composition. Thereafter, individual tray-like dental bleaching devices can be molded, such as by vacuum forming, pressing or stamping from the coated polymeric sheet and then separated into individual bleaching devices suitable for placement over a person's teeth.

Alternatively, a flowable dental bleaching composition or a substantially solid dental bleaching composition can be molded or shaped into a desired tray-like configuration comprising the bleaching layer. Thereafter, the barrier layer is attached or applied to an outer surface of the bleaching layer. In this embodiment, the barrier layer may initially comprise a flowable barrier material or precursor that is later cured or hardened, such as by removing a solvent by evaporation, by chemical or light curing, or by cooling a thermoplastic melt.

In yet another embodiment of the invention, a barrier layer in the form of a dental tray or tray-like device (e.g, a customized or non-custom tray) can be coated with a flowable dental bleaching composition. The bleaching composition is then heated together with the dental tray or otherwise allowed to dry in order to form a bleaching layer comprising a substantially solid bleaching composition. This process can be performed during commercial manufacture of the bleaching device or by an end user.

IV. Methods of Using Dental Bleaching Devices

The dental bleaching devices according to the invention can be designed to be worn for any desired time period. Increasing the concentration of dental bleaching agent generally reduces the bleaching time required to effect bleaching. Nevertheless, due to the extremely comfortable fit and reliable adhesion between the inventive dental bleaching devices and the person's teeth, it is possible to wear such devices for extended periods of time in order to ensure more uniform bleaching. They may be designed to be worn while performing normal daily activities, such as talking, eating, drinking, smoking, coughing, smiling, frowning, grimacing, or while sleeping. This greatly decreases their intrusiveness into everyday activities compared to conventional bleaching strips, which do not reliably adhere to teeth, or intrusive bleaching devices such as large, bulky bleaching dental appliances.

Dental bleaching devices according to the invention may be worn over a person's upper dental arch, lower dental arch, or both simultaneously. The ability to reliably and comfortably wear dental bleaching devices over the upper and lower dental arches simultaneously is another departure from bleaching strips, which are not recommended for use in bleaching the upper and lower dental arches at the same time.

Figure 8:
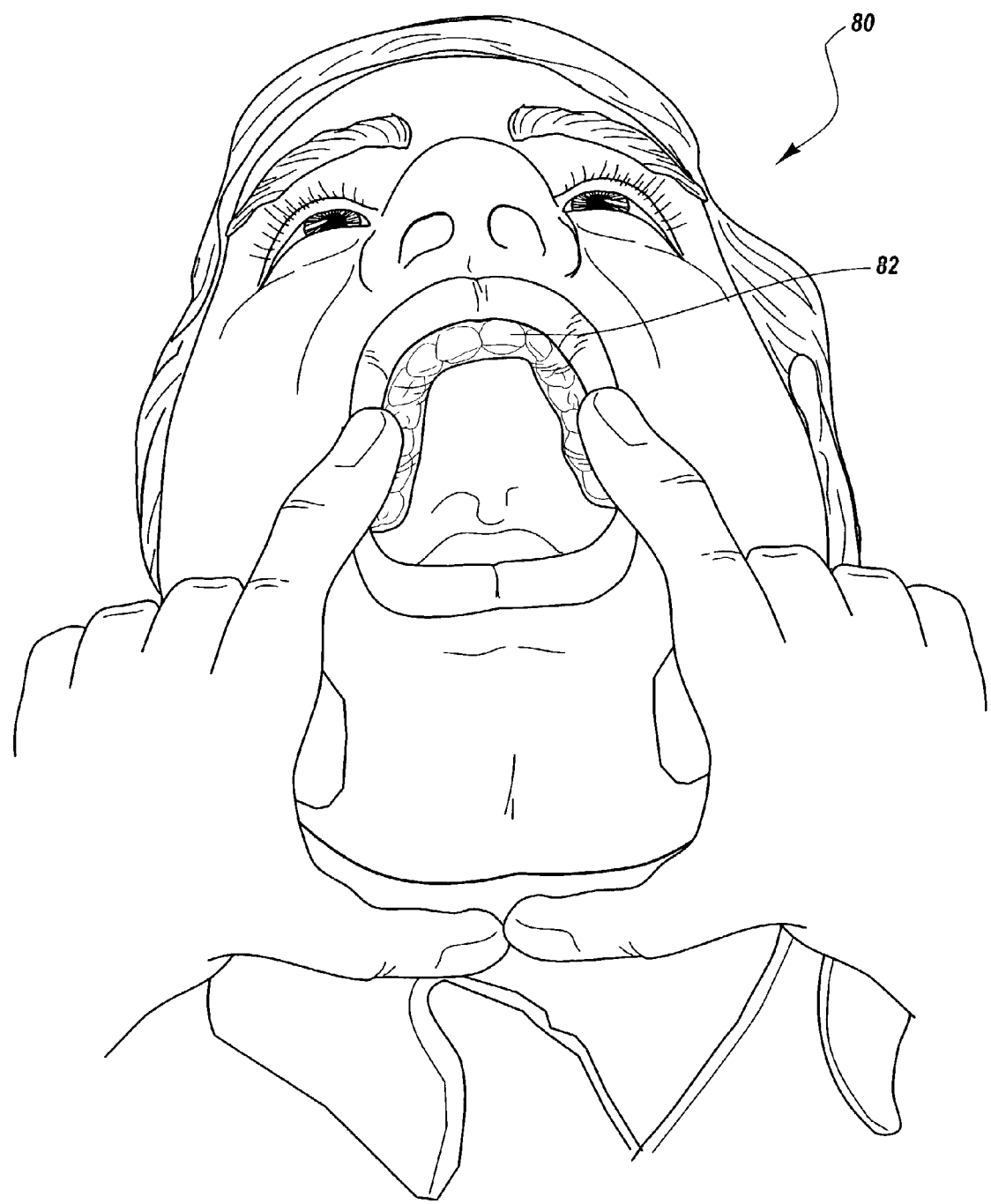
FIG. 8 illustrates a person placing a dental bleaching device according to the invention over the upper dental arch.
Figure 9:
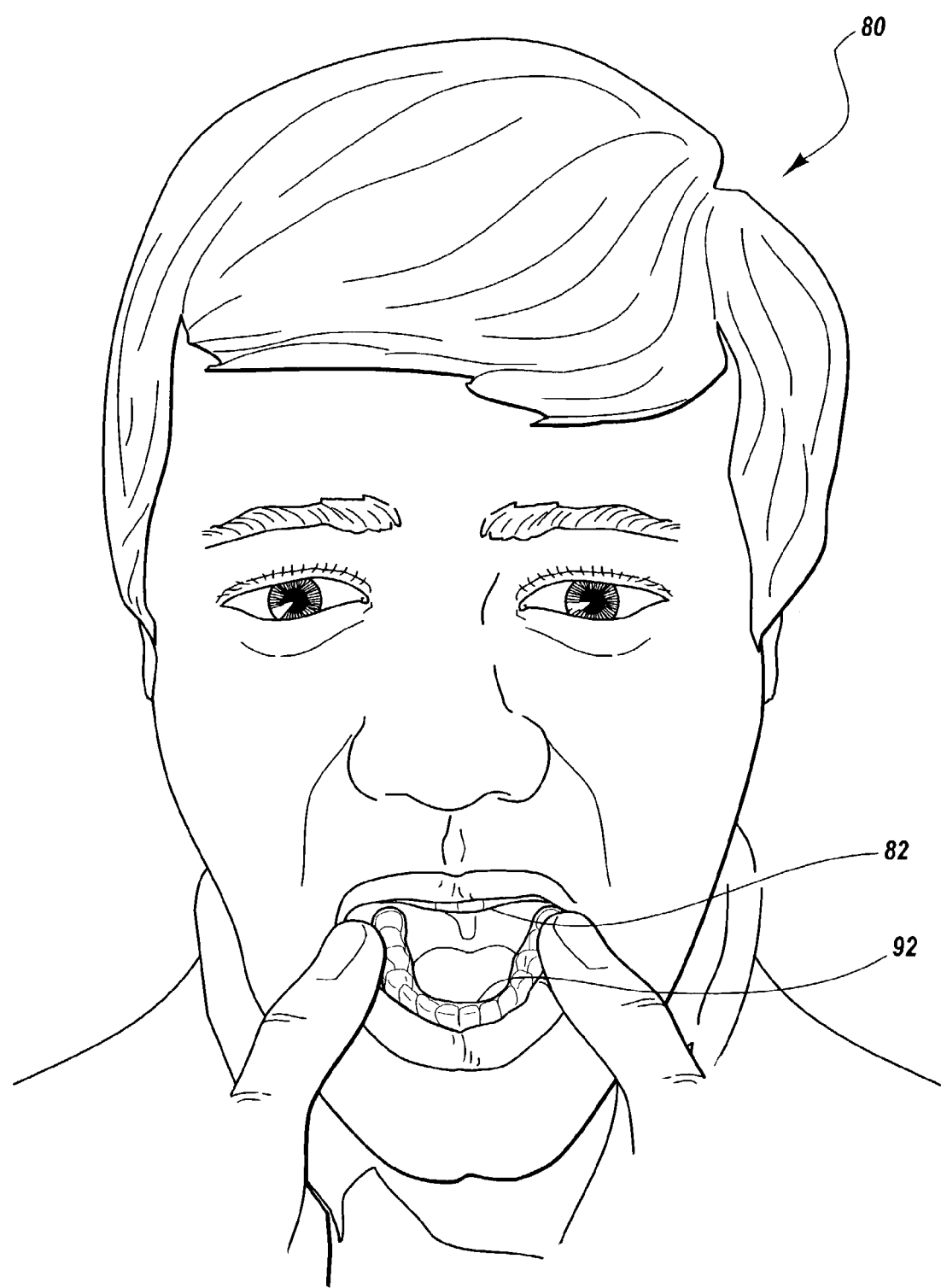
FIG. 9 illustrates a person placing a dental bleaching device according to the invention over the lower dental arch, with a dental bleaching device already placed over the upper dental arch.

FIG. 8 illustrates a person 80 placing a dental treatment device 82 over the person's upper dental arch. FIG. 9 illustrates the person 80 placing a dental treatment device 92 over the person's lower dental arch after having placed the dental treatment device 82 over the upper dental arch. It will be appreciated, however, that the dental treatment devices can be placed over a person's upper and lower dental arches in any desired order.

To remove the bleaching device, a user can pry open a corner of the barrier using a fingernail or rigid tool and then pull the remainder off. Any residual bleaching composition that remains adhered to the person's teeth can be removed by washing or flushing water over the person's teeth, and/or by brushing. Although dental bleaching compositions are very adhesive to teeth when protected from excessive moisture, they can be formulated to quickly breakdown and dissolve when flushed with excess water and/or by gentle mechanical action (e.g., brushing).

The dental bleaching devices can be worn for as little as a few minutes and as long as several hours. By way of example, not limitation, a typical bleaching session of fast duration may last from about 10 to about 30 minutes. A bleaching session of intermediate duration may last from about 30 minutes to about 2 hours. A bleaching session of long duration, including professional bleaching or overnight bleaching while a person is sleeping, may last from about 2 hours to about 12 hours.

Bleaching sessions may be repeated as many times as are needed to obtain a desired degree of whitening. In some cases, a clinical whitening effect has been observed after only 1–3 whitening sessions. A typical bleaching regimen will preferably include 1–20 bleaching sessions, more preferably 2–15 bleaching sessions, and most preferably 3–10 bleaching sessions.

V. Dental Bleaching Kits

For convenience of use, multiple dental bleaching devices may be packaged together and sold as a kit. In one embodiment, the number of dental bleaching devices provided with each kit will equal the number of sessions that represent a prescribed bleaching regimen. Because of the ease of placing the inventive dental bleaching devices over a person's teeth, coupled with the reliability with which they achieve adhesion to teeth, the likelihood that a particular bleaching device will not work as intended or fail is greatly decreased compared to conventional bleaching strips.

To efficiently utilize the space within a kit package, multiple dental bleaching devices can be stacked or interested together. The dental bleaching devices can be sealed collectively or individually as desired. A protective package 30 is depicted in FIG. 3. The bleaching devices may optionally contain a removable protective layer on an interior surface to protect the bleaching layer from contamination or moisture.

It is within the scope of the invention to provide barrier layers and bleaching composition that are initially separate and that are brought together by the end user. For example, the bleaching layer may be a dry insert comprising a dental bleaching composition that is placed into a trough of a tray-like barrier layer, with or without actually adhering the bleaching layer to the barrier layer. Alternatively, a flowable dental bleaching composition can be placed within the trough of a tray-like barrier layer and allowed to dry prior to placement of the finished dental treatment device over the person's teeth.

VI. EXAMPLES OF THE PREFERRED EMBODIMENTS

The following are several examples of dental bleaching devices that have been formulated and manufactured according to the invention. Such exemplary formulations and manufacturing conditions are given by way of example, and not by limitation, in order to illustrate dental bleaching devices that have been found to be useful for bleaching a person's teeth. Unless otherwise indicated, all percentages are by weight.

Example 1

An initially flowable dental bleaching composition suitable for use in manufacturing a substantially solid, cohesive, and non-flowable dental bleaching composition was formed by mixing together the following components:

| | |
|---|---|
| Carbamide Peroxide | 16% |
| Polyvinyl pyrrolidone (M.W. = 1.3 million) | 38% |
| Water | 46% |

The resulting bleaching composition was spread over the surfaces of three types of flexible polymer sheets: polyethylene sheets having a thickness of approximately 0.15 to 0.18 mm; sheets made of paraffin having a thickness of approximately 0.05 to 0.08 mm; and MYLAR sheets having a thickness of approximately 0.38 mm. The bleaching composition was spread using a spatula. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight to remove additional water and to determine whether prolonged heating of the dried composition would cause the carbamide peroxide bleaching agent to decompose.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch.

The tray-like dental bleaching devices were tested by placing them over a person's teeth. The residual saliva present on the tooth surfaces moistened the exposed surface of the dry dental bleaching composition and caused it to become sticky and very adhesive to teeth almost immediately. The bleaching devices were pressed against the teeth, which caused them to conform to the natural irregularities of the dental arch and adhere firmly against the teeth.

The tray-like dental bleaching devices were worn for varying time periods ranging from several minutes to several hours without becoming dislodged. The formation of oxygen bubbles within the moistened bleaching composition against the person's teeth indicated that the peroxide bleaching agent remained active and was suitable for bleaching teeth even after the bleaching composition was heated overnight in an oven. In some cases a noticeable bleaching effect was detected after just one bleaching session (e.g., a 2-hour bleaching session). In all cases, noticeable bleaching was detected after 1–3 bleaching sessions.

Example 2

An initially flowable dental bleaching composition suitable for use in manufacturing a substantially solid, cohesive, and non-flowable dental bleaching composition was formed by mixing together the following components:

| | |
|---|---|
| Carbamide Peroxide | 16% |
| PolyOx WSR 101 (M.W. = 1 million) | 7% |
| Water | 77% |

The resulting bleaching gel was spread over the surface of MYLAR sheets using a spatula. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. Unlike the bleaching composition of Example 1, the dried bleaching composition did not adhere strongly to the polymer sheets but was easily separated from the sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch.

The tray-like dental bleaching devices were tested by placing them over a person's teeth. The residual saliva present on the tooth surfaces moistened the exposed surface of the dry dental bleaching composition and caused it to become sticky and adhesive to teeth within a few seconds. The results of Example 2 indicate that, while polyethylene oxide was a satisfactory teeth adhesion agent, it was less satisfactory in promoting adhesion between a dried dental bleaching composition and a polymer sheet.

Example 3

An initially flowable dental bleaching composition suitable for use in manufacturing a substantially solid, cohesive, and non-flowable dental bleaching composition was formed by mixing together the following components:

| | |
|---|---|
| Carbamide Peroxide | 16% |
| Carbopol 974P | 5% |
| Aqueous NaOH (50%) | 6% |
| Water | 73% |

The resulting bleaching gel was spread over the surface of MYLAR sheets using a spatula. The coated sheets were heated in a forced air oven heated to a temperature of 50–70° C. for approximately 1 hour. The coated sheets were removed from the oven and inspected. Although the bleaching composition dried sufficiently to form a solid, it shrunk considerably, probably because of the large amount of water that was needed to cause Carbopol to form a gel. Shrinkage of the bleaching composition caused the polymer sheet to become partially shriveled up. Whereas shriveling of the polymer sheet was not desired, using carboxypolymethylene as a tooth adhesion agent resulted in a dried bleaching composition that adhered to a polymer sheet.

Thereafter, the coated sheets were removed from the oven after heating overnight, cut apart into smaller-sized pieces, and shaped into tray-like dental bleaching devices suitable for placement over a person's teeth. When placed over a person's teeth it took about 5 seconds for the dental bleaching composition to become moistened enough to start becoming sticky and adhesive to teeth. The dental treatment device was able to conform to the person's teeth and remain in place after being pressed against the teeth for about 30–60 seconds.

The results of Example 3 indicate that, while Carbopol 974 P is able to adhere to a MYLAR sheet and appears to be a satisfactory tooth adhesion agent once the bleaching composition is sufficiently moistened, it presents a shrinkage problem that can cause undesirable deformation of thin, flexible polymer sheets. One would expect Carbopol 974 P to work better when used with less flexible sheets and/or preformed dental trays of sufficient rigidity to avoid shriveling or unwanted deformation.

Example 4

An initially flowable dental bleaching composition suitable for use in manufacturing a substantially solid, cohesive, and non-flowable dental bleaching composition was formed by mixing together the following components:

| | |
|---|---|
| Polyethylene Oxide (M.W. = 100,000) | 20% |
| Glycerin | 2.5% |
| Sodium Percarbonate | 2.4% |
| Water | 75.1% |

The resulting bleaching gel was spread over the surface of MYLAR sheets as in Example 2. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. The bleaching composition of Example 4 did not adhere at all to the MYLAR sheets. This indicates that the lower molecular weight polyethylene oxide of Example 4 was even less adhesive to MYLAR sheets than the higher molecular weight polyethylene oxide of Example 2. Sheets comprising a solid layer of the bleaching composition of Example 2 could also be formed by spreading the composition on a solid surface such as glass, drying the composition, and then peeling off the dried composition.

By comparison, when the bleaching composition of Example 1 was applied to a glass surface and then dried, it adhered so strongly that it could not readily be peeled off the glass surface. Instead, it had to be forcefully chipped or pried off using a razor blade.

The dried bleaching composition of Example 4 did, however, adhere to a person's teeth when moistened, although not as well as the bleaching compositions of Examples 1–3. This indicates that the composition of Example 4 might have commercial application in a tray-like dental bleaching device to the extent that problems adhering to the barrier layer are overcome or are not an issue.

Example 5

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Water | 25% |
| Ethanol | 25% |
| Polyvinyl pyrrolidone (M.W. = 1.3 million) | 38% |
| Glycerin | 73% |

The resulting bleaching composition was spread over the surfaces of polyethylene, paraffin, and MYLAR sheets as described in Example 1. The coated sheets were heated in a forced air oven heated to a temperature of 50–70° C. for approximately 45 minutes. The coated sheets were removed from the oven and inspected. The bleaching composition had dried sufficiently so as to form a solid, coherent layer of bleaching layer on the surface of the polymer sheets. Using a mixture of water and ethanol as the solvent allowed the bleaching composition to dry in less than time than the compositions of Examples 1–4. The inclusion of glycerin helped the bleaching composition remain more flexible and less brittle after drying. The dried bleaching composition adhered well to each of the polymer sheets. After initial drying, the coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

Example 6

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Water | 21% |
| Ethanol | 21% |
| Kollidon VA 64 (M.W. = 60,000) | 40% |
| Carboxy methyl cellulose | 3% |
| PEG 600 | 5% |

Kollidon VA 64 is a polyvinyl pyrrolidone polymer sold by BASF. The resulting bleaching composition was spread over the surfaces of polyethylene, paraffin, and MYLAR sheets as described in Example 1. The coated sheets were heated in a forced air oven heated to a temperature of 50–70° C. for approximately 45 minutes. The coated sheets were removed from the oven and inspected. The bleaching composition had dried sufficiently so as to form a solid, coherent layer of bleaching layer on the surface of the polymer sheets.

The inclusion of polyethylene glycol helped the bleaching composition remain more flexible and less brittle after drying. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

Example 7

An initially flowable dental bleaching composition suitable for use in manufacturing a substantially solid, cohesive, and non-flowable dental bleaching composition was formed by mixing together the following components:

| | |
|---|---|
| Carbamide Peroxide | 11.6% |
| Ethanol | 55.8% |
| Kollidon VA 90 F (M.W. = 1.3 million) | 24.4% |
| Carboxy methyl cellulose | 2.3% |
| PEG 600 | 5.8% |

The resulting bleaching composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The bleaching composition had dried sufficiently so as to form a solid, coherent layer of bleaching layer on the surface of the polymer sheets. Using ethanol as the only solvent allowed the bleaching composition to dry in even less time than the compositions of Examples 5 and 6. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

Example 8

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Ethanol | 65% |
| Kollidon VA 90 F (M.W. = 1.3 million) | 20% |
| PEG 600 | 5% |

The resulting bleaching composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

Example 9

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Ethanol | 64% |
| Kollidon VA 90 F (M.W. = 1.3 million) | 25% |
| PEG 600 | 1% |

The resulting bleaching composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

Example 10

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Ethanol | 64% |
| Kollidon VA 90 F (M.W. = 1.3 million) | 23% |
| PEG 600 | 1% |
| Aerosil 200 | 2% |

The resulting bleaching composition was spread over the surfaces of polyethylene, paraffin, and MYLAR sheets as described in Example 1. Aerosil 200 was added as a tackifying agent to promote adhesion of the wet bleaching composition to the polymer sheets. The coated sheets were heated in a forced air oven heated to a temperature of 50–70° C. for approximately 30 minutes. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

Example 11

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Ethanol | 66.9% |
| Kollidon VA 90 F (M.W. = 1.3 million) | 20% |
| PEG 600 | 0.1% |
| Aerosil 200 | 3% |

The resulting bleaching composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

Example 12

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| PolyOx (M.W. = 1 million) | 7.5% |
| Water | 75.5% |
| Glycerin | 5% |
| Aerosil 200 | 2% |

The resulting bleaching gel was spread over the surface of MYLAR sheets as in Example 2. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. The bleaching composition of Example 12 did not adhere well to the MYLAR sheets. It also shrunk somewhat after extended drying. The dried bleaching composition of Example 12 was able to adhere to a person's teeth when moistened.

Example 13

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Kollidon 90 F (M.W. = 1.3 million) | 10% |
| Kollidon 30 (M.W. = 50,000) | 20% |
| Water | 53% |
| Glycerin | 5% |
| Aerosil 200 | 2% |

The resulting bleaching composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

Example 14

An initially flowable dental bleaching composition suitable for use in manufacturing a substantially solid, cohesive, and non-flowable dental bleaching composition was formed by mixing together the following components:

| Carbamide Peroxide | 10% |
| Kollidon 90 F (M.W. = 1.3 million) | 27% |
| Water | 50% |
| Glycerin | 7% |
| Aerosil 200 | 6% |

The resulting bleaching composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

Example 15

An initially flowable dental bleaching composition suitable for use in manufacturing a substantially solid, cohesive, and non-flowable dental bleaching composition was formed by mixing together the following components:

| Carbamide Peroxide | 10% |
| Kollidon 90 F (M.W. = 1.3 million) | 28% |
| Water | 50% |
| Glycerin | 7% |
| Aerosil 200 | 5% |

The resulting bleaching composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental bleaching device in the shape of a dental tray suitable for placement over a person's teeth in order to carry out dental bleaching, comprising:
    a barrier layer comprising a moisture-resistant material in the shape of a dental tray comprising a front side wall, a rear side wall, and a trough between said front and rear side walls; and
    a bleaching layer within said trough comprising a substantially solid dental bleaching composition having a first surface adjacent to said barrier layer and a second surface that has increased adhesiveness to teeth when moistened by saliva or water, said bleaching layer being in the shape of a dental tray and having a rigidity so as to at least partially contribute to maintaining said dental bleaching device in the shape of a dental tray piror to placing said bleaching device over a person's teeth, said dental bleaching composition comprising:
        at least one dental bleaching agent; and
        at least one tooth adhesion agent that at least partially contributes to said increased adhesiveness to teeth when said dental bleaching composition is moistened by saliva or water.

2. A dental bleaching device as defined in claim 1, said bleaching layer comprising a single coherent mass in the shape of a dental tray comprising a front side wall, a rear side wall, and a trough between said front and rear side walls.

3. A dental bleaching device as defined in claim 1, said bleaching layer contributing more to maintaining said dental bleaching device in the shape of a dental tray than said barrier layer prior to use.

4. A dental bleaching device as defined in claim 1, said barrier layer being flexible so that it will readily conform to the shape of a person's teeth when said dental bleaching device is in use.

5. A dental bleaching device as defined in claim 1, said bleaching layer comprising a plurality of spaced-apart coherent masses.

6. A dental bleaching device as defined in claim 1, said barrier layer having a rigidity so as to at least partially contribute to maintaining said dental bleaching device in the shape of a dental tray prior to placing said bleaching device over a person's teeth.

7. A dental bleaching device as defined in claim 6, said barrier layer contributing more to maintaining said dental bleaching device in the shape of a dental tray than said bleaching layer prior to and during use.

8. A dental bleaching device as defined in claim 1, said barrier layer being inilially horseshoe shaped prior to use so that said dental bleaching device at least approximately conforms to a person's dental arch with minimal longitudinal shaping.

9. A dental bleaching device as defined in claim 1, said barrier layer initially having a longitudinal curvature that is less than the curvature of a person's dental arch prior to use so that additional longitudinal curving of said dental bleaching device is required what said dental bleaching device is placed over a person's teeth.

10. A dental bleaching device as defined in claim 1, said barrier layer initially having a substantially straight/longitudinal profile prior to use so that longitudinal curving of said dental bleaching duvice is required when said dental bleaching device is placed over a person's teeth.

11. A dental bleaching device as defined in claim 1, at least a portion of said trough having an approximate U-shaped cross section.

12. A dental bleaching device as defined in claim 1, at least a portion of said trough having an approximate V-shaped cross section.

13. A dental bleaching device as defined in claim 1, at least a portion of said trough having an approximate L-shaped cross section.

14. A dental bleaching device as defined in claim 1, at least a portion of said trough having approximately a rectangular or trapezoidal cross section.

15. A dental bleaching device as defined in claim 1, said barrier layer comprising at least one polyolefin.

16. A dental bleaching device as defined in claim 15, said polyolefin comprising at least one of polyethylene, high density polyethylene, low density polyethylene, ultra-low density polyethylene, polypropylene, or polytetrafluoroethylene.

17. A dental bleaching device as defined in claim 1, said barrier layer comprising at least one of wax, metal foil, paraffin, ethylene-vinyl acetate copolymer, ethylene-vinyl alcohol copolymer, polycaprolactone, polyester, polycarbonate, polyurethane, polyamide, or polyesteramide.

18. A dental bleaching device as defined in claim 1, said dental bleaching agent comprising at least one of carbamide peroxide, metal peroxide, percarbonate, perborate, peroxy acid, peroxy acid salt, chlorite, or hypochlorite.

19. A dental bleaching device as defined in claim 1, said dental bleaching agent having a concentration in a range of about 5% to about 80% by weight of said dental bleaching composition.

20. A dental bleaching device as defined in claim 1, said dental bleaching agent having a concentration in a range of about 10% to about 60% by weight of said dental bleaching composition.

21. A dental bleaching device as defined in claim 1, said dental bleaching agent having a concentration in a range of about 20% to about 50% by weight of said dental bleaching composition.

22. A dental bleaching device as defined in claim 1, said tooth adhesion agent comprising polyvinyl pyrrolidone.

23. A dental bleaching device as defined in claim 1, said tooth adhesion agent comprising at least one or carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

24. A dental bleaching device as defined in claim 1, said tooth adhesion agent having a concentration in a range of about 10% to about 90% by weight of said dental bleaching composition.

25. A dental bleaching device as defined in claim 1, said tooth adhesion agent having a concentration in a range of about 20% to about 80% by weight of said dental bleaching composition.

26. A dental bleaching device as defined in claim 1, said tooth adhesion agent having a concentration in a range of about 40% to about 75% by weight of said dental bleaching composition.

27. A dental bleaching device as defined in claim 1, said dental bleaching composition further comprising at least one non-volatile solvent.

28. A dental bleaching device as defined in claim 1, wherein said dental bleaching device is sized and configured so as to fit over at least a portion of a person's upper dental arch.

29. A dental bleaching device as defined in claim 1, wherein said dental bleaching device as sized and configtued so as to fit over at least a porlion of a person's lower dental arch.

30. A dental bleaching device as defined in claim 1, wherein said barrier layer has a cross-sectional thickness in a range of about 0.025 mm to about 1.5 mm.

31. A dental bleaching device as defined in claim 1, wherein said bleaching layer has a cross-seclional thickness in a range of about 0.1 mm to about 3 mm.

32. A dental bleaching device as defined in claim 31, wherein said bleaching layer has a cross-sectional thickness in a range of about 0.1 mm to about 0.5 mm.

33. A dental bleaching device as defined in claim 31, wherein said bleaching layer has a cross-sectional thickness in a range of about 0.5 mm to about 2 mm.

34. A dental bleaching device as defined in claim 31, wherein said bleaching layer has a cross-sectional thickness in a range of about 2 mm to about 3 mm.

35. A dental bleaching device as defined in claim 1, wherein said barrier layer is sized and configured so as to approximately terminate at or near a person's gingival margin when said dental bleaching device is in use.

36. A dental bleaching device as defined in claim 1, wherein said dental bleaching device is contained within a scaled package prior to use.

37. A kit for use in bleaching a person's teeth comprising a plurality of dental bleaching devices according to claim 1.

38. A kit as defined in claim 37, wherein at least some of said dental bleaching devices are stacked and internested together.

39. A kit as defined in claim 37, wherein said kit includes from 3 to 10 dental bleaching devices.

40. A method for bleaching a person's teeth comprising obtaining a dental bleaching device according to claim 1 and then placing said dental bleaching device over at least a poition of the person's teeth for a desired time period.

41. A dental bleaching device in the shape of a dental tray suitable for placement over a person's teeth in order to carry out dental bleaching, comprising:
   a thin, flexible barrier layer comprising a moisture-resistant material; and
   a bleaching layer adjacent said barrier layer and comprising a substantially solid dental bleaching composition in the shape of a dental tray comprising a front side wall, a rear side wall, and a trough between said front and rear side walls, the bleaching layer having a rigidity so that said bleaching layer contributes more to maintaining said dental bleaching device in the shape of a dental tray prior to use than said barrier layer, said bleaching composition having increased adhesiveness to teeth when moistened by saliva or water, said bleaching composition comprising:
at least one dental bleaching agent; and
at least one tooth adhesion agent that at least partially contributes to said increased adhesiveness to teeth when said dental bleaching composition is moistened by saliva or water.

42. A dental bleaching device as defined in claim 41, at least a portion of said trough having a cross section that is approximately U-shaped, V-shaped, L-shaped, rectangular, or trapezoidal.

43. A dental bleaching device in the shape of a dental tray suitable for placement over a person's teeth in order to carry out dental bleaching, comprising:
a barrier layer comprising a moisture-resistant polymeric material in the shape of a dental tray comprising a front side wall, a rear side wall, and a trough between said front and rear side walls; and
a bleaching layer within said trough comprising a substantially solid dental bleaching composition having a first surface adjacent to at least one of said front side wall or rear side wall and a second surface that has increased adhesiveness to teeth when moistened by saliva or water, said bleaching layer having a rigidity so as to at least partially contribute in maintaining said dental bleaching device in the shape of a dental tray prior to placing said bleaching device over a person's teeth said dental bleaching composition comprising:
at least one dental bleaching agent; and
at least one tooth adhesion agent that at least partially contributes to said increased adhesiveness to teeth when said dental bleaching composition is moistened by saliva or water.

44. A dental bleaching device as defined in claim 43, at least a potion of said trough having a cross section that is approximately U-shaped, V-shaped, L-shaped, rectangular, or trapezoidal.

45. A method for bleaching a person's teeth, comprising:
(a) obtaining a dental bleaching device in the shape of a dental tray comprising a front side wall, a rear side wall, and a trough between said front and rear side walls, the dental bleaching device further comprising:
an outer barrier layer comprising a moisture-resistant material; and
a bleaching layer comprising a substantially solid dental bleaching composition having increased adhesiveness to teeth when moistened by saliva or water, said bleaching layer having a rigidity so as to at least partially contribute in maintaining said dental bleaching device in the shape of a dental tray prior to placing said bleaching device over a person's teeth, said dental bleaching composition comprising:
at least one dental bleaching agent; and
at least one tooth adhesion agent that at least partially contributes to said increased adhesiveness to teeth when said dental bleaching composition is moistened by saliva or water;
(b) moistening an exposed surface of said bleaching layer so as to increase adhesiveness of said bleaching layer to teeth; and
(c) placing said dental bleaching device over at least a portion of the person's teeth for a desired time period, the moistened bleaching layer adhering and retaining said dental bleaching device against the person's teeth during the desired time period.

46. A method for bleaching a person's teeth as defined in claim 45, wherein (b) is performed by applying water or an aqueous solution to said exposed surface.

47. A method for bleaching a person's teeth as defined in claim 45, wherein (b) is performed by allowing residual saliva on the person's teeth to moisten said exposed surface as the dental bleaching device is placed over the person's teeth.

48. A method for bleaching a person's teeth as defined in claim 45, further comprising removing said dental bleaching device and any remaining dental bleaching composition.

49. A method for bleaching a person's teeth as defined in claim 48, said dental bleaching device being removed about 10 to about 30 minutes after being placed over the person's teeth.

50. A method for bleaching a person's teeth as defined in claim 48, said dental bleaching device being removed about 30 minutes to about 2 hours after being placed over the person's teeth.

51. A method for bleaching a person's teeth as defined in claim 48, said dental bleaching device being removed about 2 hours to about 12 hours after being placed over the person's teeth.

52. A method for bleaching a person's teeth as defined in claim 45, at least a portion of said trough of said dental bleaching device having a cross section that is approximately U-shaped, V-shaped, L-shaped, rectangular, or trapezoidal.

53. A dental bleaching device as defined in claim 43, said barrier layer having a rigidity so that said barrier layer contributes more to maintaining said dental bleaching device in the shape of a dental tray prior to use than said bleaching layer.

* * * * *

UNITED STATES PATENT AND TRADEMARK OFFICE
CERTIFICATE OF CORRECTION

PATENT NO. : 7,074,042 B2
APPLICATION NO. : 10/446235
DATED : July 11, 2006
INVENTOR(S) : Allred et al.

It is certified that error appears in the above-identified patent and that said Letters Patent is hereby corrected as shown below:

Column 1
Line 13, after "(e.g., by" remove "a"

Column 4
Line 56, after "the teeth to" insert --be--

Column 9
Line 24, change "provides" to --provided--

Column 14
Line 30, change "an" to --can--
Line 37, after "teeth to" insert --be--
Line 52, change "generally" to --general--

Column 27
Line 6, change "inilially" to --initially--
Line 14, after "required" change "what" to --when--
Line 17, change "straight/longitudinal" to --straight longitudinal--
Line 19, change "duvice" to --device--

Column 28
Line 23, change "configtued" to --configured--
Line 30, change "cross-secliional" to --cross-sectional--

UNITED STATES PATENT AND TRADEMARK OFFICE
CERTIFICATE OF CORRECTION

PATENT NO. : 7,074,042 B2
APPLICATION NO. : 10/446235
DATED : July 11, 2006
INVENTOR(S) : Allred et al.

It is certified that error appears in the above-identified patent and that said Letters Patent is hereby corrected as shown below:

Column 29
Line 33, change "teeth" to --teeth,--
Line 40, change "potion" to --portion--

Signed and Sealed this

Twenty-second Day of May, 2007

JON W. DUDAS
*Director of the United States Patent and Trademark Office*